(12) United States Patent
van de Water et al.

(10) Patent No.: US 7,884,326 B2
(45) Date of Patent: Feb. 8, 2011

(54) MANIPULATOR FOR ROTATING AND TRANSLATING A SAMPLE HOLDER

(75) Inventors: Jeroen van de Water, Breugel (NL); Johannes van den Oetelaar, Eindhoven (NL); Raymond Wagner, Gorinchem (NL); Hendrik Nicolaas Slingerland, Venlo (NL); Jan Willem Bruggers, Eindhoven (NL); Adriaan Huibert Dirk Ottevanger, Malden (NL); Andreas Schmid, Berkeley, CA (US); Eric A. Olson, Champaign, IL (US); Ivan G. Petrov, Champaign, IL (US); Todor I. Donchev, Urbana, IL (US); Thomas Duden, Kensington, CA (US)

(73) Assignees: FEI Company, Hillsboro, OR (US); The Board of Trustees of the University of Illinois, Urbana, IL (US); The Regents of the University of California, Oakland, CA (US)

( * ) Notice: Subject to any disclaimer, the term of this patent is extended or adjusted under 35 U.S.C. 154(b) by 534 days.

(21) Appl. No.: 11/861,721

(22) Filed: Sep. 26, 2007

(65) Prior Publication Data
US 2008/0173813 A1 Jul. 24, 2008

(30) Foreign Application Priority Data
Jan. 22, 2007 (EP) ................................. 07100942
Apr. 18, 2007 (EP) ................................. 07106400

(51) Int. Cl.
*G01N 23/00* (2006.01)
*G21K 7/00* (2006.01)
*H02K 41/00* (2006.01)

(52) U.S. Cl. ................ 250/311; 250/310; 250/442.11; 250/491.1; 74/490.08; 310/323.27; 310/323.17; 310/12.14; 310/40 R; 219/121.82; 318/687

(58) Field of Classification Search ................ 250/306, 250/307, 309–311, 440.11, 442.11, 491.1, 250/492.2, 492.3; 310/317, 323.01–323.03, 310/323.06, 323.17, 323.27, 328, 330, 12.01, 310/12.05, 12.14, 40 MM, 40 R; 74/490.08, 74/490.13, 496; 219/121.82; 318/687
See application file for complete search history.

(56) References Cited
U.S. PATENT DOCUMENTS
3,307,035 A 2/1967 Grasenick et al.
4,019,109 A 4/1977 McCoy et al.

(Continued)

FOREIGN PATENT DOCUMENTS
EP 1863066 12/2007

(Continued)

*Primary Examiner*—Bernard E Souw
(74) *Attorney, Agent, or Firm*—Scheinberg & Griner, LLP; Michael O. Scheinberg; David Griner

(57) ABSTRACT

A manipulator for use in e.g. a Transmission Electron Microscope (TEM) is described, said manipulator capable of rotating and translating a sample holder (4). The manipulator clasps the round sample holder between two members (3A, 3B), said members mounted on actuators (2A, 2B). Moving the actuators in the same direction results in a translation of the sample holder, while moving the actuators in opposite directions results in a rotation of the sample holder.

29 Claims, 3 Drawing Sheets

U.S. PATENT DOCUMENTS

| | | | |
|---|---|---|---|
| 4,507,597 A | 3/1985 | Trost | |
| 4,785,177 A | 11/1988 | Besocke | |
| 4,797,261 A | 1/1989 | Swann et al. | |
| 5,089,708 A | 2/1992 | Asselbergs | |
| 5,986,270 A | 11/1999 | Bormans et al. | |
| 6,246,060 B1* | 6/2001 | Ackeret et al. | 250/442.11 |
| 6,252,333 B1 | 6/2001 | Iino et al. | |
| 6,388,262 B1 | 5/2002 | Alani et al. | |
| 6,635,887 B2 | 10/2003 | Kwan et al. | |
| 6,819,029 B2 | 11/2004 | Ohno et al. | |
| 6,841,788 B1 | 1/2005 | Robinson et al. | |
| 6,849,989 B2 | 2/2005 | Schmid et al. | |
| 6,855,926 B2* | 2/2005 | Palmer et al. | 250/305 |
| 6,963,068 B2* | 11/2005 | Asselbergs et al. | 250/311 |
| 7,005,636 B2 | 2/2006 | Tappel | |
| 7,034,316 B2 | 4/2006 | Wagner et al. | |
| 7,381,968 B2 | 6/2008 | Tanaka et al. | |
| 7,511,282 B2 | 3/2009 | Agorio et al. | |
| 2003/0010911 A1* | 1/2003 | Palmer et al. | 250/306 |
| 2004/0144924 A1* | 7/2004 | Asselbergs et al. | 250/311 |
| 2004/0178372 A1 | 9/2004 | Rasmussen | |
| 2004/0185586 A1* | 9/2004 | Yasutake et al. | 438/14 |
| 2005/0035302 A1 | 2/2005 | Morrison | |
| 2006/0219919 A1* | 10/2006 | Moore et al. | 250/311 |
| 2008/0250881 A1 | 10/2008 | Dona | |
| 2008/0302961 A1* | 12/2008 | Tashiro et al. | 250/310 |
| 2009/0146075 A1 | 6/2009 | Schmid et al. | |

FOREIGN PATENT DOCUMENTS

| | | |
|---|---|---|
| EP | 1868225 | 12/2007 |
| JP | 62236692 | 10/1987 |
| JP | 3281188 | 12/1991 |
| JP | 04206333 | 7/1992 |
| JP | 5200638 | 8/1993 |
| JP | 08106873 | 4/1996 |
| JP | 09236755 | 9/1997 |
| JP | 2002319364 | 10/2002 |
| JP | 2002334818 | 11/2002 |
| JP | 2003065745 | 3/2003 |
| JP | 2003115527 | 4/2003 |
| JP | 2004223673 | 8/2004 |
| JP | 2005026467 | 1/2005 |
| WO | 9620495 | 7/1996 |
| WO | 9959192 | 11/1999 |
| WO | 2008051880 | 5/2008 |

* cited by examiner

MANIPULATOR FOR ROTATING AND TRANSLATING A SAMPLE HOLDER

The invention described and claimed herein was made in part utilizing funds supplied by the U.S. Department of Energy under Contract No. DE-AC02-05CH11231. The Government has certain rights in this invention.

The invention relates to a manipulator for rotating a sample holder round a rotation axis and translating said sample holder along a translation axis, said sample holder showing at least one outer surface with rotational symmetry round the rotation axis, the so-named driven surface, the manipulator comprising a base, and multiple members, each member showing a surface, the so-named driving surface, each of the driving surfaces movable with respect to the base along the translation axis, and actuators to move the members with respect to the base.

The invention also relates to a stage comprising such a manipulator and an apparatus comprising such a manipulator.

Such a manipulator is known from U.S. Pat. No. 6,849,989 B2.

Such a manipulator is used in an apparatus where very accurate manipulation is required, such as in a Scanning Probe Microscope (SPM) or a Transmission Electron Microscope (TEM).

The known manipulator is used for translating and/or rotating a cylindrical body, e.g. a sample holder.

The manipulator comprises a base surrounding the sample holder and two sets of three piezoelectric actuators, each actuator pointing inwards from the base, each actuator showing a surface, the so-named driving surface, contacting the sample holder. Each set of three surfaces is disposed round the sample holder, e.g. 120 degrees apart from each other, and the surfaces clasp the sample holder between them. Thereby the sample holder is fixed between the surfaces. The actuators are capable of translating the driving surfaces with respect to the base along a translation axis and also in a direction perpendicular to the translation axis.

By moving the driving surfaces along the translation axis, the sample holder is translated, and by moving the driving surfaces perpendicular to the translation axis, the sample holder may be rotated round the translation axis.

It is noted that rotation axis and translation axis coincide, while the actuators are equipped to move along two axis: one parallel to the translation axis and one perpendicular to the translation axis.

The manipulator does not show any slippage in bearings when operating (only rolling of the sample holder over the driving surfaces occurs), and therefore very small movements can be realized without stick/slip effects and the related irregularity in movement.

The known manipulator has only a limited stroke before at least one of the driving surfaces has to break contact with the sample holder. Although scaling the dimensions of the manipulator can scale the stroke along the translation axis, the rotational stroke is very limited e.g. less than +/−1 degrees.

The known patent document describes that the known manipulator can increase its stroke by moving the actuators slowly in one direction, whereby static friction between driving surfaces and sample holder keeps the driving surfaces on the same position on the sample holder, and then moving the actuators quickly in the opposite direction. As a result of the quick movement the driving surfaces slip over the sample holder and the driving surfaces are thus repositioned with respect to the sample holder.

The invention aims to provide an alternative manipulator.

To that end the manipulator according to the invention is characterized in that the actuators are linear actuators equipped to cause a movement along the translation axis, at least two driving surfaces face each other, and the driving surfaces are equipped to clasp the driven surface between them, as a result of which the sample holder rotates round the rotation axis when the at least two driving surfaces are moved along the translation axis over an equal distance in opposite directions, and the sample holder is translated parallel to the translation axis when the driving surfaces are moved along the translation axis over an equal distance in the same direction, and as a result of which the rotation axis and the translation axis are perpendicular to each other.

As the rotational stroke is now given by the relative stroke of the driving surfaces with respect to each other in relation to the circumference of the driven surface, the rotational stoke can be in excess of 360 degrees when the relative movement of the driving surfaces is in excess of the circumference of the driven surface, without the need to reposition the driving surfaces with respect to the driven surface.

The members can e.g. take the form of two parallel cylinders, between which the sample holder is clamped. By displacing the cylinders with respect to the base, a translation and/or rotation of the sample holder with respect to the base is realized.

The driving surfaces can be substantially parallel, but can also be formed such that at least at the end of the stroke of the driving surfaces the surfaces are non-parallel so that the driven surface cannot slip from the driving surfaces, which could result in the loss of the sample holder.

It is noted that U.S. Pat. No. 6,388,262 B1 also describes a manipulator capable of rotation over more than 360 degrees. This manipulator comprises a round sample holder which is actuated with a thin metal band, and small bearings. The total number of parts is rather large. As the dimensions for this type of manipulators is quite small (typically approximately 5 mm wide), the resultant construction is very fragile and prone to damage.

It is also noted that another advantage of the manipulator according to the invention is that the sample holder is from at least one side freely accessible. This enables easy insertion and extraction of the sample holder from the manipulator.

In an embodiment of the manipulator according to the invention the driving surfaces are substantially parallel to each other when the driven surface is clasped between the driving surfaces.

In another embodiment of the manipulator according to the invention the number of driving surfaces is an even number, each driving surface facing another driving surface, each set of driving surfaces facing each other equipped to clasp a driven surface between them.

In a further embodiment of the manipulator according to the invention the number of driving surfaces equals two.

This is the minimum number of driving surfaces that can be used, and thus provides the simplest construction. By forming the members as e.g. two long cylinders, and equipping the driven surface with a circular groove, the sample holder can be kept between the two long cylinders. The rotation axis is in this embodiment along the rotational symmetry axis of the sample holder.

In another embodiment of the manipulator according to the invention the number of driving surfaces equals four, and in which the sample holder has two protruding sample holder axles, said sample holders axles in line with each other, each sample holder axle clasped between two of the four driving surfaces.

In this embodiment the rotational axis is along the axis of the sample holder axles.

In yet another embodiment of the manipulator according to the invention the members take the form of generalised cylinders.

It is noted that a generalized cylinder can have a circular cross-section, but that the cross-section can also be an ellipse or any other given curve.

In a further embodiment of the manipulator according to the invention the cylinders are tapering cylinders, the side of the tapering cylinders facing the base having a larger cross-section than the side of the tapering cylinders near the sample holder.

Inventors found that when the members are straight cylinders, the manipulator may show a high sensitivity to vibrations. This is due to the high-Q bending modes associated with such cylindrical shapes. When such a cylinder showing a high-Q is exposed to excitation in the form of vibration with all kinds of frequencies (also known as white noise) this results in a oscillating movements of the cylinders with a high peak-to-peak amplitude. By giving the cylinders a tapered form the inventors found that higher resonance frequencies and lower Q-values can be achieved, resulting in movement with a lower peak-to-peak amplitude when exposed to white noise.

In an embodiment of the manipulator according to the invention the linear actuators are piezoelectric linear actuators.

Piezoelectric linear actuators are known to be available with a small step size and a long stroke, making them well-suited as actuators for a manipulator according to the invention. Examples of such actuators are e.g. the "Nanomotor®" manufactured by Dr. Volker Klocke Nanotechnik, Aachen, Germany.

In another embodiment of the manipulator according to the invention the manipulator is equipped to operate in vacuum.

The manipulator as described need not use lubricants or other materials which are incompatible vacuum. This makes the manipulator suited as a manipulator in a particle-optical apparatus such as a Transmission Electron Microscope (TEM), an apparatus known per se.

It is noted that the area where a sample resides in a TEM is typically evacuated to a pressure of $10^{-6}$ mbar or less. Many lubricants and e.g. synthetic materials are incompatible with this pressure.

In yet another embodiment of the manipulator according to the invention the driving surfaces are shaped to cooperate with the shape of the driven surface, the cooperating shapes being concave rims on the driving surfaces and a convex rim on the sample holder.

To keep the sample holder between the driving surfaces, it is necessary to form the cooperating driving and driven surfaces such that the sample holder cannot slip or fall from the manipulator. By shaping the surfaces with cooperating convex and concave surfaces, this is achieved.

In a further embodiment of the manipulator according to the invention the driving surfaces are shaped to cooperate with the shape of the driven surface, the cooperating shapes being convex rims on the driving surfaces and a concave rim on the sample holder.

In yet a further embodiment of the manipulator according to the invention the concave rim is a groove and the convex rim is an edge.

In another embodiment of the manipulator according to the invention the manipulator is mounted on a stage, the stage showing a flange for mounting the stage on an apparatus and the stage showing a mounting base on which the base of the manipulator is mounted, the stage capable of moving the mounting base with respect to the flange.

By mounting the manipulator on a stage, such as a conventional stage used in a TEM, the manipulator obtains additional degrees of freedom (DoF's), enabling more versatile positioning of the sample holder.

In a further embodiment of the manipulator according to the invention the manipulator is mounted on a stage of which the mounting base of the stage is moved with respect to the flange of the stage along at least two translational axes and round one rotational axis, said axes not coinciding with the axes of the manipulator, thereby resulting in a stage equipped to manipulate a sample holder with respect to the flange with five degrees of freedom.

The manipulator according to the invention shows two degrees of freedom (DoF's): one rotational and one translational. Many applications demand that the sample holder can be positioned with more DoF's. By mounting the base of the manipulator on a conventional stage, the sample holder can be positioned with more than two DoF's.

In yet another embodiment of the manipulator according to the invention the manipulator is mounted on a stage of which the mounting base is moved with respect to the flange of the stage along at least two translational axes and round at least one rotational axis, one of the translation axis of the manipulator coinciding with one of the translational axis of the stage.

In this embodiment the base of the manipulator is mounted on a conventional stage. The translation of the manipulator may be used as e.g. a fine adjustment of the sample holders position in that direction, while the translation of the conventional stage in that direction may be used as a coarse movement.

In still another embodiment an apparatus is equipped with the manipulator according to the invention.

In this embodiment the manipulator is mounted on an apparatus, such as a Transmission Electron Microscope (TEM), a Scanning Transmission Electron Microscope (STEM), a Scanning Electron Microscope (SEM), a Focussed Ion Beam (FIB) machine.

The manipulator can also be mounted in or on other apparatus, such as a Scanning Probe Microscope (SPM). SPM is the generic name for a group of instrument comprising Atomic Force Microscope (AFM), Scanning Tunnelling Microscope (STM), Scanning Near-field Optical Microscope (SNOM).

All these instruments can analyse samples with nanometre resolution or better, and employ manipulators/stages that position the sample or sample holder with nanometre accuracy.

The invention is now further elucidated on the basis of schematic drawings, in which corresponding features are identified by identical numerals. To this end:

Figure 1A:
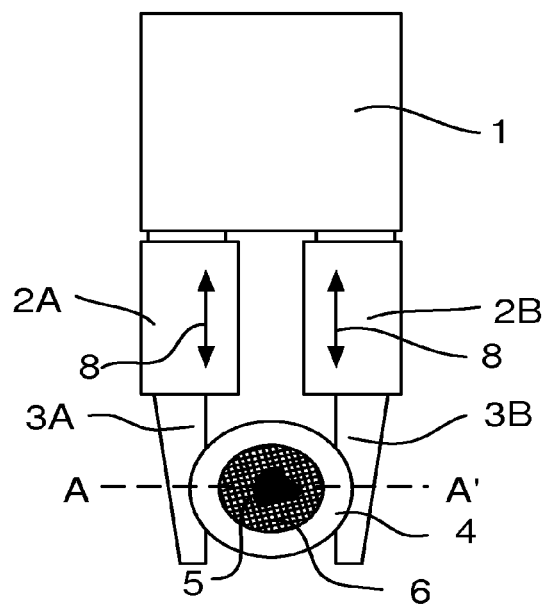
FIG. 1A shows a manipulator according to the invention with a sample holder.

FIG. 1A shows a manipulator according to the invention with a sample holder. A base 1 is connected to two actuators 2A and 2B. Two members in the form of two tapering cylinders 3A and 3B are attached to the actuators.

The actuators are equipped to displace the members along an axis 8. The actuators can be piezoelectric actuators, but may also be motors, or may e.g. operate on thermal expansion and shrinking.

Between the members 3A, 3B a sample holder 4 is clasped. Each member shows a driving surface where the member may be in contact with the sample holder, while the sample holder shows a driven surface where the sample holder may be in contact with the driving surfaces.

The sample holder shows a grid 6 on which a sample 5 is placed. Sample holder 4 shows a grid (or at least a surface showing at least partial transparency) to enable e.g. charged particles as used in a TEM to pass at least locally through the grid.

However, sample holders equipped with a thin film are also known to be used in TEM. Other applications, such as X-ray microscopy, may result in other demands to the sample holder, resulting in e.g. a different form of the sample holder.

When the actuators 2A, 2B cause the members 3A, 3B to displace over the same distance and in the same direction, the sample carrier 4 is translated along the direction in which the actuators move.

When the actuators cause the members to move in opposite directions (and over the same distance) the sample carrier 4 is rotated.

Obviously, when the distances over which the members 3A, 3B are moved are not identical, a combined rotation and translation of the sample carrier 4 results.

It is noted that, as mentioned before, the members 3A, 3B are best formed as tapering cylinders to avoid high-Q vibrational sensitivity, but cylinders may be used as well.

Figure 1B:
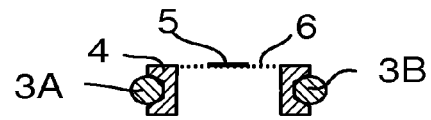
FIG. 1B shows a cross-section of the manipulator of FIG. 1A along line AA'.

FIG. 1B shows a cross-section of the manipulator of FIG. 1A along line AA'.

Here it is shown clearly that members 3A and 3B show a circular cross-section, cooperating with a groove in the sample holder. The sample carrier can thereby roll over the driving surfaces of the members, while the sample carrier is kept in the plane defined by the two members. Therefore there is no risk of the sample carrier escaping from the two members. That the driven surface rolls over the driving surfaces result in a frictionless or almost frictionless movement, and avoids the slip/stick effects and the irregular movement associated with a movement in which friction occurs.

It is noted that, although the members are shown with a circular cross-section, the person skilled in the art will readily recognise that members with another cross-section, such as a square cross-section, may be used.

Figure 1C:
FIG. 1C shows a cross-section along line AA' of the manipulator of FIG. 1A with an alternative sample holder.

FIG. 1C shows a cross-section along line AA' of the manipulator of FIG. 1A with an alternative sample holder.

The shown sample holder provides compatibility with the standard sample grids. The grid 6 is inserted in the sample carrier and secured with a circular spring 7 to prevent it from escaping.

It is noted that in this embodiment the rotation axis is perpendicular to the plane in which the grid 6 and thus sample 5 are mounted.

Figure 2A:
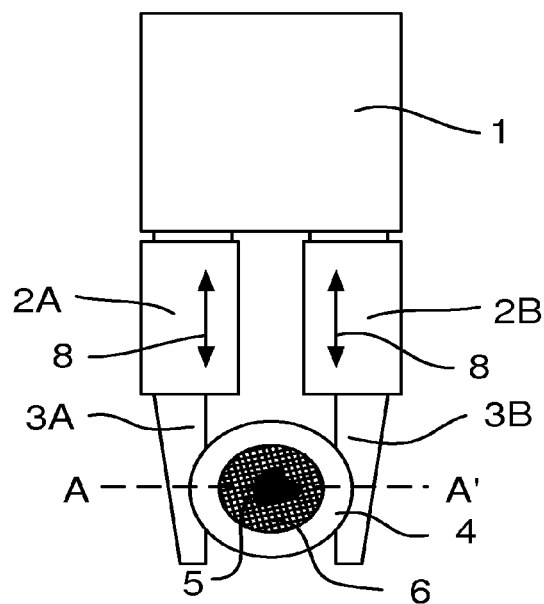
FIG. 2A shows an alternative manipulator according to the invention with a sample holder.

FIG. 2A shows an alternative manipulator according to the invention with a sample holder.

FIG. 2A can be though to be derived from FIG. 1A. Here however the members 3A, 3B show a groove and the sample carrier shows a cooperating rim.

Figure 2B:
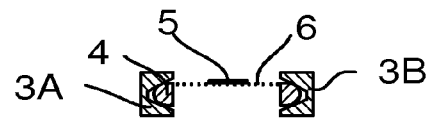
FIG. 2B shows a cross-section of the manipulator of FIG. 2A along line AA'.

FIG. 2B shows a cross-section of the manipulator of FIG. 2A along line AA'.

Figure 3A:
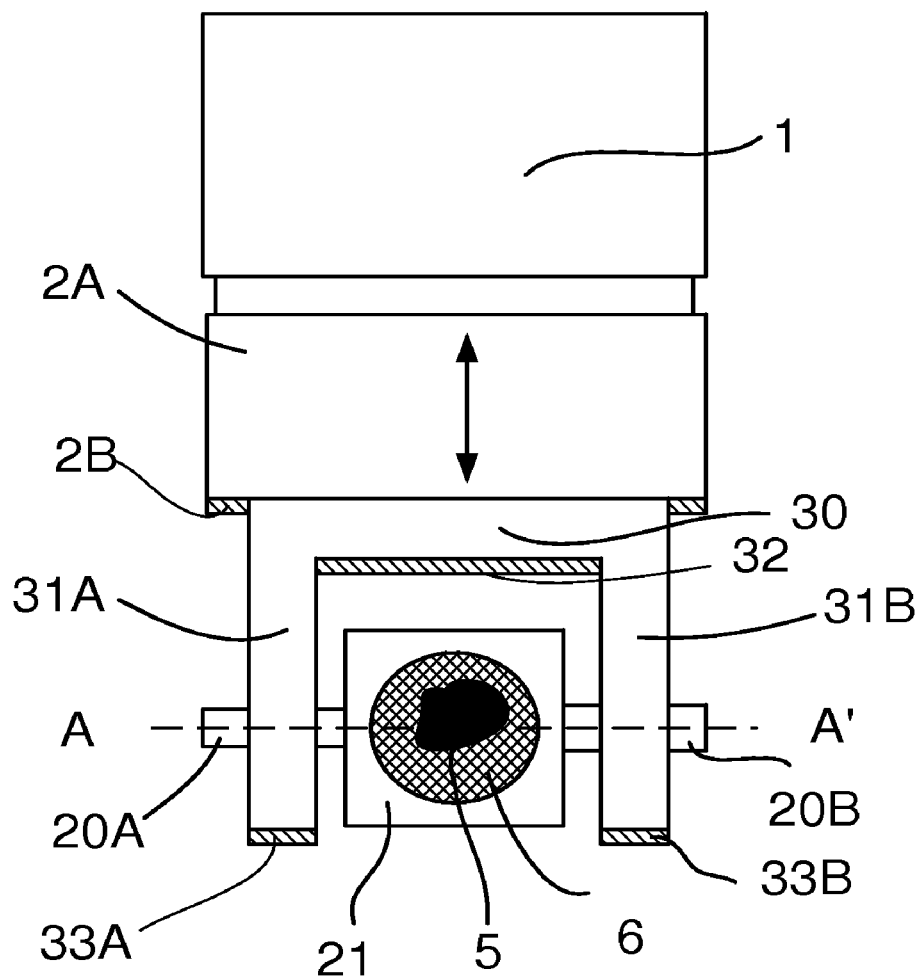
FIG. 3A shows a manipulator in which a sample holder with two protruding axles is clamped between four driving surfaces.

FIG. 3A shows a manipulator in which a sample holder with two protruding axles is clamped between four driving surfaces.

FIG. 3A shows a base 1 on which two actuators 2A, 2B are mounted. Actuator 2B, shown hatched, is in this figure slightly longer than actuator 2A. To each actuator 2A, 2B a member is connected. Member 30 is connected to actuator 2A and member 32 (shown hatched) is connected to actuator 2B. Member 30 has two extremities, 31A and 31B, and member 32 has two extremities 33A and 33B (shown hatched).

The sample holder 21 shows two axles, 20A and 20B, arranged along a common axis. A grid 6 is mounted on the sample holder. A grid 6 is mounted on the sample holder 21, on which a sample 6 is placed.

Axle 20A of sample holder 21 is clasped between extremities 31A and 33A, while axle 20B of the sample holder is clasped between the extremities 31B and 33B.

Figure 3B:
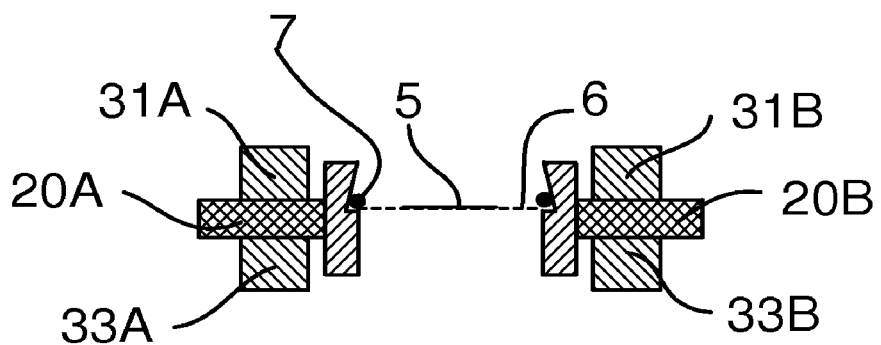
FIG. 3B shows a cross-section of the manipulator of FIG. 3A along line AA'.

FIG. 3B shows a cross-section along line AA'. It shows the extremities 31A and 33B between which axle 20A is clasped, and extremities 31B and 33B between which axle 20B is clasped.

As shown grid 6 is held in place by a circular spring 7.

By moving actuator 2A in one direction and actuator 2B in the other direction over an equal length (with respect to the base 1), extremities 31A and 31B will move in one direction with respect to the sample holder and extremities 33A and 33B in the opposite direction. A rotation of axles 20A and 20B with respect to the base results, and thus a rotation of the sample holder.

By moving both actuators in the same direction (over the same length) with respect to base 1, a translation of the sample holder (with respect to the base) results.

It is noted that in this embodiment the rotation axis is along the plane of the grid 6 and sample 5.

It is further noted that in this embodiment the driving surfaces of extremities 31A, 31B, 33A and 33B are shown as flat surfaces, and that the extremities have a rectangular cross-section. The person skilled in the art will recognize that a manipulator according to the invention need not be limited to this form, but that also extremities with e.g. circular or elliptic cross-section can be used.

Figure 4:
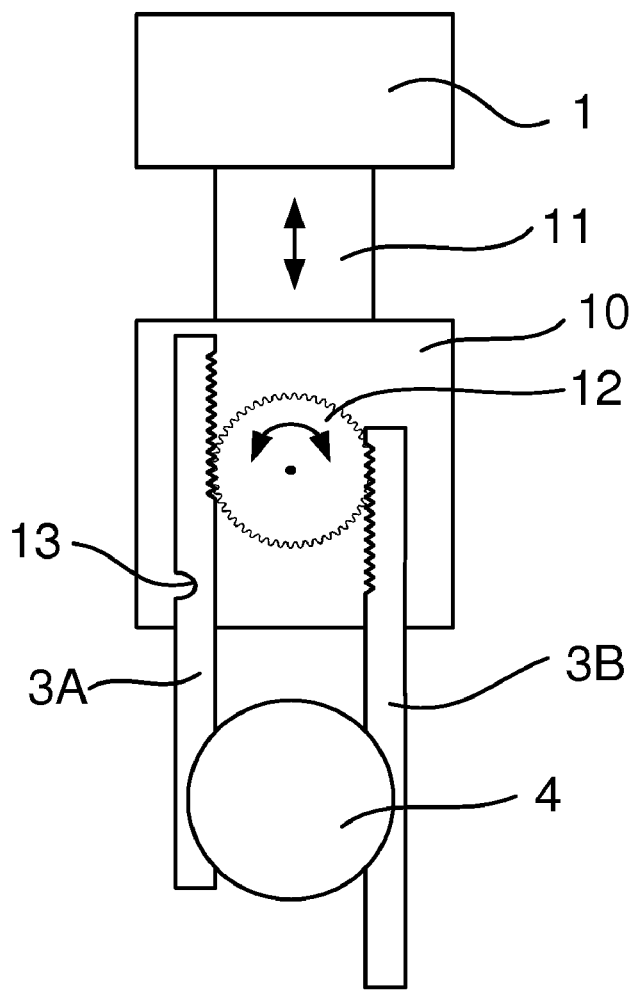
FIG. 4 shows an alternative manipulator according to the invention.

FIG. 4 shows an alternative manipulator according to the invention.

FIG. 4 shows a base 1, on which a linear actuator 11 is mounted. The actuator 11 can move a sub-base 10. On sub-base 10 a gear wheel 12 is mounted, which acts as actuator for members 3A and 3B. Hereby the translation of actuator 11 results in a translation of the sample holder 4, while a rotation of gear wheel 12 results in a rotation of the sample holder.

A thinning in member 3A acts as a combined hinge and spring, enabling clamping of the sample holder with a controlled force by pre-loading of the spring. It is noted that the person skilled in the art will recognise that the pre-loading of the members can also be realised without such a hinge.

Figure 5:
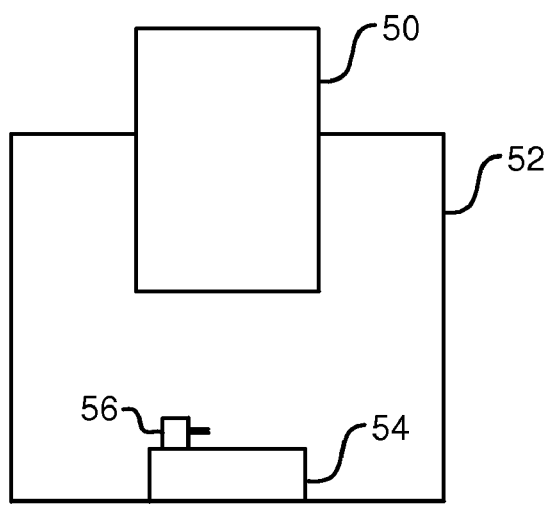
FIG. 5 shows an apparatus including a manipulator of the present invention.

FIG. 5 shows a microscopic processing apparatus 50, which can comprise, for example, a charged particle beam system, such as a TEM, an STEM, an SEM, or a FIB machine, or an SPM. The term microscopic processing apparatus is used herein to include any system used for imaging and processing microscopic samples. Such instruments typically include a sample stage 54, moveable with multiple degrees of freedom, for example, x and y translation and tilt. A manipulator 56 of the present invention can be attached to sample stage 54 to provide additional degrees of freedom to position the sample within the field of view of apparatus 50 for observation or processing. Charged particle beam systems require that the sample be positioned within a vacuum chamber 52 for observation or processing, and manipulator 56 is therefore typically positioned within the vacuum chamber on such systems.

By mounting a base of the manipulator on a conventional stage, e.g. a stage such as is used in a TEM, a stage with more degrees of freedom can be made. Such a stage can then be used in a particle-optical apparatus, such as in a TEM.

Although in the embodiments only a TEM is mentioned, the person skilled in the art will recognize that instead of a TEM, the invention may also be used as the stage of a Scanning Electron Microscope (SEM), a Focused Ion Beam (FIB instrument), and the like. Also for use in a Scanning Probe Microscope (SPM), which is the generic name of a family of instruments comprising Scanning Tunneling Microscopes (STM's), Scanning Near-field Optical Microscopes (SNOM's), and the like, the manipulator according to the invention can be used.

We claim:

1. Manipulator for rotating a sample holder round a rotation axis and translating said sample holder along a translation axis, said sample holder showing at least one outer surface with rotational symmetry round the rotation axis, the so-named driven surface, the manipulator comprising:
    a base,
    multiple members, each member showing a surface, the so-named driving surface, each of the driving surfaces movable with respect to the base along the translation axis, and
    actuators to move the members with respect to the base, characterized in that
    the actuators are linear actuators equipped to cause a movement along the translation axis,
    at least two driving surfaces face each other, and
    the driving surfaces are equipped to clasp the at least one driven surface between them,
    as a result of which the sample holder rotates round the rotation axis when the at least two driving surfaces are moved along the translation axis over an equal distance in opposite directions, and the sample holder is translated parallel to the translation axis when the driving surfaces are moved along the translation axis over an equal distance in the same direction, and as a result of which the rotation axis and the translation axis are perpendicular to each other.

2. The manipulator according to claim 1 in which the driving surfaces are substantially parallel to each other when the driven surface is clasped between the driving surfaces.

3. The manipulator according to claim 1 in which the number of driving surfaces is an even number, each driving surface facing another driving surface, each set of driving surfaces facing each other equipped to clasp a driven surface between them.

4. The manipulator according to claim 3 in which the number of driving surfaces equals two.

5. The manipulator according to claim 3 in which the number of driving surfaces equals four, and in which the sample holder has two protruding sample holder axles, said sample holder axles in line with each other, each sample holder axles clasped between two of the four driving surfaces.

6. The manipulator according to claim 1 in which the members take the form of generalised cylinders.

7. The manipulator according to claim 6 in which the cylinders are tapering cylinder, the side of the tapering cylinders facing the base having a larger cross-section than the side of the tapering cylinders near the sample holder.

8. The manipulator according to claim 6 in which the linear actuators are piezoelectric linear actuators.

9. The manipulator according to claim 1 equipped to operate in vacuum.

10. The manipulator according to claim 1 in which the driving surfaces are shaped to cooperate with the shape of the driven surface, and in which the cooperating shapes are concave rims on the driving surface and a convex rim on the sample holder.

11. The manipulator according to claim 1 in which the driving surfaces are shaped to cooperate with the shape of the driven surface, and in which the cooperating shapes are convex rims on the driving surface and a concave rim on the sample holder.

12. The manipulator according to claim 10 in which concave rim is a groove and the convex rim is an edge.

13. The manipulator according to claim 1 in which the manipulator is mounted on a stage, the stage showing a flange for mounting the stage on an apparatus and the stage showing a mounting base on which the base of the manipulator is mounted, the stage capable of moving the mounting base with respect to the flange.

14. The manipulator according to claim 13, in which the mounting base of the stage is moved with respect to the flange along least two translational axes and round one rotational axis, each of the translational axes substantially perpendicular to the other translational axes and each of the rotational axes substantially perpendicular to the other rotational axis, resulting in a manipulator equipped to manipulate a sample holder with respect to the flange with five degrees of freedom.

15. The manipulator according to claim 13, in which the mounting base of the stage is moved with respect to the flange along at least two translational axes and round at least one rotational axis, at least one of the translation axis of the manipulator substantially coinciding with one of the translational axis of the stage.

16. Apparatus equipped with the manipulator according to claim 1.

17. The apparatus according to claim 16, in which the apparatus comprises a vacuum chamber and in which the manipulator is located in said vacuum chamber.

18. The apparatus according to claim 17, in which the vacuum chamber is part of a particle-optical apparatus.

19. A manipulator for translating and rotating a sample holder for holding a microscopic sample, comprising;
    a base;
    multiple arms extending substantially parallel to each other from the base, each arm having a longitudinal axis and having a first driving surface facing a second driving surface on an opposing arm, the first and second driving surfaces supporting the sample holder; and
    one or more actuators for moving the multiple arms along their longitudinal axes, such that when the arms are moved an equal distance in the same direction, the sample holder is translated without rotation in the direction of the longitudinal axis, and when the arms are moved an equal distance in opposite directions, the sample holder is rotated without translation.

20. The manipulator of claim 19 in which the one or more actuators comprise one or more piezoelectric actuators.

21. The manipulator of claim 19 in which one or more of the multiple arms comprises a tapered cylinder.

22. The manipulator of claim 19 further comprising a circularly shaped sample holder and in which the multiple arms include two arms for supporting and rotating the circularly shaped sample holder between them, the sample holder and the multiple arms including mating surfaces to maintain the sample holder between the arms during movement of the arms.

23. The manipulator of claim 22 in which the sample holder comprises a sample holder for a transmission electron microscope.

24. The manipulator of claim 19 further comprising a sample holder having axles extending from opposite sides of the sample holder and in which the multiple arms include four arms, two sets of two arms each, each set grasping an axle extending on either side of a work piece holder, such that when an arm in each set moves relative to the other arm in the set, the axle rotates, rotating the sample holder.

25. A microscope, comprising;
   a chamber for containing a sample during operation of the microscope; and
   a manipulator in accordance with claim 19 located within the chamber for positioning the sample within the microscope.

26. The microscope of claim 25 in which the chamber is a vacuum chamber.

27. The microscope of claim 25 in which the microscope is a transmission electron microscope, a scanning transmission electron microscope, a scanning electron microscope, a focused ion beam machine or a scanning probe microscope.

28. A method of observing a sample in a microscope, comprising:
   providing a manipulator for manipulating a sample under the microscope, the manipulator including:
      a base;
      multiple arms extending substantially parallel to each other from the base, each arm having a longitudinal axis and having a first driving surface facing a second driving surface on an opposing arm, the first and second driving surfaces supporting the sample holder; and
      one or more actuators for moving the multiple arms along their longitudinal axes, such that when the arms are moved an equal distance in the same direction, the sample holder is translated without rotation in the direction of the longitudinal axis, and when the arms are moved an equal distance in opposite directions, the sample holder is rotated without translation;
   positioning the work piece in contact with the first and second driving surfaces;
   driving the two arms to position the sample within the microscope; and
   observing the sample using the microscope.

29. The method of claim 26 in which providing a manipulator for manipulating a sample under the microscope includes providing the manipulator within a vacuum chamber of an electron microscope or a focused ion beam system.

* * * * *